United States Patent [19]

Tamers

[11] 4,315,890

[45] Feb. 16, 1982

[54] DEVICE FOR THE IDENTIFICATION OF VOLATILE FLUIDS

[75] Inventor: Murry A. Tamers, Hialeah, Fla.

[73] Assignee: Intersci Corporation, Miami, Fla.

[21] Appl. No.: 145,447

[22] Filed: May 1, 1980

[51] Int. Cl.³ ............ G01N 1/22; G01N 21/29; G01N 31/22

[52] U.S. Cl. ............... 422/58; 422/59; 422/61; 422/80; 422/86

[58] Field of Search .......... 422/58, 56, 59, 61, 422/100, 84, 85, 86, 80

[56] References Cited

U.S. PATENT DOCUMENTS

| | | | |
|---|---|---|---|
| 3,068,855 | 12/1962 | Furlong, Jr. | 422/58 X |
| 3,286,506 | 11/1966 | Lloyd | 422/86 X |
| 3,388,975 | 6/1968 | Wallace | 422/86 X |
| 3,741,727 | 6/1973 | Stroterhoff | 422/58 X |
| 4,042,336 | 8/1977 | Larsson | 422/58 |
| 4,071,319 | 1/1978 | Nugent | 422/59 |
| 4,138,474 | 2/1979 | Updike | 422/58 X |
| 4,195,057 | 3/1980 | Patel | 422/56 |

Primary Examiner—Ronald Serwin

[57] ABSTRACT

A device is used in a chemical analysis of substances containing volatile components wherein the volatile component sought to be identified is volatilized off for reaction with a reagent to produce a color change or the like which indicates the presence of the volatile component.

11 Claims, 5 Drawing Figures

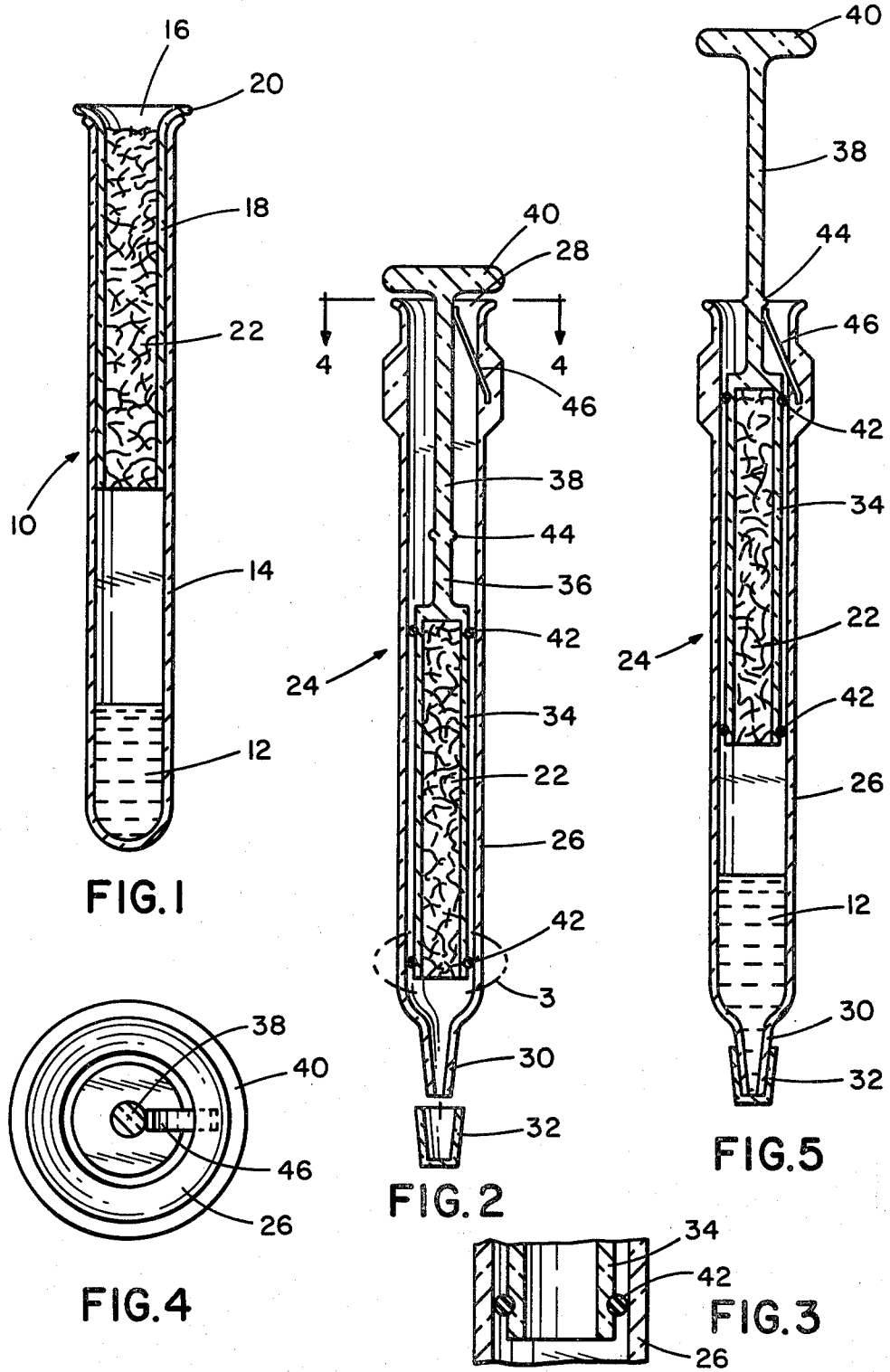

DEVICE FOR THE IDENTIFICATION OF VOLATILE FLUIDS

The present invention relates generally to an analytical system for determination of the presence of a volatile component within a specimen, and it relates more particularly to a device for the analysis of biological samples and particularly to a device for determining the presence of volatile organic compounds in body fluids. The analysis can be performed easily by individuals with little or no familiarity with chemical techniques.

The presence of volatile components in a fluid sample is determined with reagents which react with the vapor to indicate the presence and often the amounts thereof in the sample. The device can be cleaned and reused after each analysis. The device is simple in construction and easy in operation and because of the low cost of the device, it can be used as a single use test device which can be discarded after use.

SUMMARY OF THE INVENTION

The invention is of particular use in chemical analyses which must be performed routinely at a moderate cost. Specifically, the present invention is a diagnostic tool in the detection of low concentrations of volatile organic compounds, such as alcohols or ketones, which normally are not present in body fluids.

The invention comprises two concentrically placed members: a container, such as a conventional test tube, and a cylinder. A fluid sample is placed in the container. The cylinder is packed with an absorbant material which contains indicating reagents, and the cylinder is positioned within the tube. Glass wool is a suitable absorbant material. As the sample is heated, the volatile fraction distills and condenses or otherwise reacts with the reagent within the cylinder. In a second embodiment, the vaporization is achieved under vacuum with or without moderate heating. The indicating reagents in the cylinder permit a direct determination of the presence of the volatile material and the concentration thereof in the specimen.

It is an object of this invention to provide a simple device for the routine analysis of the types described, in which the device is inexpensive and the analysis can be performed with minimal instruction in laboratory procedures and in which the analysis can be automated to decrease costs and to reduce the possibility of human error in the sample preparation and analysis.

Other objects and advantages will be apparent from the following detailed description made with reference to the accompanying drawings.

BRIEF DESCRIPTION OF THE DRAWINGS

FIG. 1 is a sectional view of the device of the present invention;

FIG. 2 is a sectional view of a second embodiment of the device adapted for distillation under a partial vacuum;

FIG. 3 is a sectional view of the second embodiment taken along the line 3—3 of FIG. 2;

FIG. 4 is a partial sectional view taken about the line 4—4 of FIG. 2; and

FIG. 5 is a sectional view of the device of FIG. 2 with the plunger in the extended position to create a partial vacuum.

DETAILED DESCRIPTION

FIG. 1 illustrates a device generally designated by the numeral 10 for the analysis of one or more components in a fluid sample 12. A container 14 in the form of a test tube having an opening 16 at one end and sealed at the other end holds the sample which can include blood, urine, a similar biological fluid or a liquid composition such as an organic liquid. A hollow cylinder 18, which is open at both ends, is inserted in telescoping relation within the container 14; the outside diameter of the cylinder 18 is slightly less than the inside diameter of the container 14 so that the cylinder fits close to the inner wall of the container. The container should be formed of a heat resistant material such as glass, or a plastic which is inert to the materials being tested.

The cylinder 18 includes a flange 20 which, when the cylinder is inserted within the container 14, engages the edge of the opening 16 to support the cylinder within the container with the lower open end of the cylinder spaced from the bottom of the container. The flange 20 also serves as a fingerhold for the removal of the cylinder from the container.

In the operation of the invention, the sample 12 is placed in the bottom of the container 14. The cylinder 18 is filled with a lightly packed mass of inert absorbant material, such as glass wool 22, which functions as a matrix on which a chemical reagent in the form of a solution is retained as by surface tension. The reagent solution, as will be described in more detail, is used as an indicating means in the analysis. The cylinder 18 is then inserted within the container 14 such that no part of the cylinder is in direct contact with the sample 12.

The portion of the container 14 below the cylinder 18 is heated to a temperature sufficient to effect volatilization of the component of the sample sought to be detected. The preferred heating temperature is slightly higher than the boiling point or azeotropic boiling point of the compound to be analyzed. For example, an ethanol-water azeotrope boils at 78.2° C. Therefore, the preferred heating temperature in an ethanol analysis is at least 80° C.

The sample can be heated by any conventional heat source. For example, electrical resistance heaters or steam heating is suitable in a laboratory, but for a non-laboratory analysis a portable heating unit may be advantageous. In the preferred practice of the invention use is made of a hot water bath or other fluid bath or dry bath in which the container can be partially immersed to the desired level.

Referring to FIG. 2, a device designated by the numeral 24 is shown for effecting a partial vacuum to enable volatization at a lower temperature, such as room temperature or slightly above. A container 26 has an opening 28 at one end and an open protruding tip 30 at the other end. The open end is adapted to be sealed by a removable cap 32.

The device 24 includes a cylinder 34 that is similar to the cylinder 18 of FIG. 1. The cylinder 34, however, is also adapted to embody the elements of a plunger 36 capable of axial displacement within the container 26 to create a partial vacuum therein. The cylinder 34 is connected to a rod element 38 dimensioned to have a length to extend beyond the open end 28 with the outwardly extending portion being provided with a handle 40 for actuation on the cylinder 34. O-rings 42 effect a sealing engagement between the outer surface of the cylinder 34 and the inner surface of the container 26 to provide an air-tight seal between the cylinder and the container 26. (See FIG. 3). Other close-fitting sliding seals can also be used.

In the operation of this embodiment, the cap 32 is removed from the top 30 before insertion of the tip into the sample fluid. The plunger 36 is then partially withdrawn from the container 26 to admit sample fluid 12 into the container through the tip and thereafter the cap 32 is applied to seal the tip 30. In carrying out the test, the plunger 36 is withdrawn further to create subatmospheric conditions within the container portion holding the sample. Means are provided for latching the plunger in its withdrawn position to maintain the desired exposure of the sample to subatmospheric conditions. In the illustrated modification, such latching means comprises a ring 44 about the rod element 38 which is engaged by a flexible metal strip 46 that is supported by the container 26 when in extended position. (See FIG. 5). In this manner, the plunger remains in an extended position to maintain a partial vacuum in the container.

The sample is then heated as previously described. The presence of a vacuum within the container lowers the volatilization temperature so that only a moderate heating of the sample is required to achieve volatilization.

The container 26 can be lengthened to increase the stroke of the plunger further to reduce the subatmospheric pressure with corresponding reduction in volatilization temperature. With longer reaction times, no heating is necessary.

The cylinders of both embodiments are made of materials inert to the fluids and vapors and they are preferably made of glass, plastic or other transparent or translucent material to enable see-through for color change of the reagent. For example, the solution for detecting alcohols includes sulfuric acid and potassium dichromate, for which glass cylinders are best suited.

Each cylinder can be constructed of a synthetic material, but under such circumstances it may often be desirable to make use of a glass or silicon sleeve inserted within the cylinder to prevent contact of the indicating reagents with the cylinder. Resistant plastics may be used or the reagent containing cylinder may be refrigerated to decrease the reaction or decomposition rate.

The indicating reagents for the detection of alcohols include oxidizing agents, such as chromate ($Cr_2O_7^=$), and alcohol dehydrogenases. For example, alcohols can be distinguished from many other classes of compounds upon oxidation of chromate and aqueous sulfuric acid: within several seconds, the orange solution turns blue-green due to the formation of low oxidation state chromic salts. An aqueous solution of 10 molar sulfuric acid and 0.02 molar $K_2Cr_2O_7$ produces detectable and reproducible color changes in this invention.

Visual observation of the color change within the cylinder and height of the color change is often sufficient to determine the concentration of the volatile component. The precision and sensitivity of the analysis, however, can be improved by eluting the reagents after the reaction and determining the extent of color change spectrophotometrically or placing the detection tube directly in a spectrophotometer.

The present invention can be used to analyze any fluid in which the component to be detected volatilizes off at a lower temperature than other substances in the fluid. The detection of ethyl alcohol is only one example of the use of this invention. For example, the water content of fluids can be readily determined. The cylinder can contain a hydroscopic material, such as anhydrous magnesium perchlorate ($Mg(ClO_4)_2$), barium oxide (BaO), anhydrous calcium sulfate ($CaSO_4$) or calcium chloride ($CaCl_2$). The cylinder is weighed before and after the heating of the sample; the difference in weight is the water content of the sample.

The presence of ketones in the sample can interfere with a positive alcohol test. Therefore, when an alcohol test is performed, it is often necessary to verify that the color change is not due to the presence of a ketone. Under such circumstances the cylinder or the bottom portion of the tube can be coated with a reagent which reacts with ketones to produce an immediate, characteristic color change. Representative of such reagents are sodium nitroferricyanide and ferric chloride.

Having described the basic concepts of the present invention, reference is now made to the following examples, which are provided to illustrate and not to limit the practice of this invention.

EXAMPLE 1

The apparatus of FIG. 1 was used in determining the concentration of ethyl alcohol in a human urine sample. The container 14 had a length of 100 mm, an inside diameter of 11 mm and an outside diameter of 13 mm. The cylinder 18 had a length and an outside diameter of 70 mm and 10 mm, respectively. Approximately 2 milliliters (ml) of the urine sample was placed in the container leaving a space of 20 mm between the top of the sample and the bottom of the cylinder.

The cylinder was filled with glass wool which had absorbed 0.75 ml of an indicating solution comprising 0.02 Molar (M) potassium dichromate in 10 M sulfuric acid. The sample was heated for 15 minutes at 110° C. The bottom three-fourths of the indicating solution retained by the glass wool changed from the original yellow to blue. The color changes of standard solutions containing known quantities of ethyl alcohol were determined. A comparison of the color change and height of the color change in the present analysis indicated an ethyl alcohol concentration of 0.20% by volume in the urine.

EXAMPLE 2

The method of Example 1 was repeated. After another urine sample was heated under the same conditions, the bottom one-half of the indicating solution changed to a green color. A comparison of the color change with that of standard solutions indicated an ethyl alcohol concentration of 0.10% by volume in the urine.

EXAMPLE 3

The method of Example 1 was repeated with a urine sample which was shown by independent analysis to contain no ethyl alcohol. After the sample was heated at the same temperature for the same length of time, the indicating solution did not change color. Even after heating for one hour at 110° C., the solution remained yellow.

EXAMPLE 4

To detect the presence of a ketone in the sample, the bottom portion of the container was coated with 10 mg sodium nitroferricyanide and 10 mg lithium hydroxide. An immediate darkening of a urine sample occurred when the sample was added to the container. The resultant red coloration indicated the presence of a ketone. A spectrophotometric analysis showed an acetone concentration of 0.05% by volume.

The material being tested may be in the form of a solid containing a volatile component, preferably in finely divided particulate form whereby the material can be poured into the container through the open end before the inner tube provided with supported reactant is inserted through the open end of the container. Thus the term fluid, as used herein and in the claims, is intended to include solid as well as liquid samples which may contain a volatile component sought to be determined.

It will be understood that various changes and modifications can be made in the above described apparatus without departing from the spirit thereof, particularly as defined in the following claims.

What is claimed is:

1. A naturally volatile substance identification device comprising:
   a. a container for receiving a solid or liquid specimen and;
   b. detecting means within the container spaced from the bottom of the container, said detecting means including:
      i. an inert absorbant element, contained within an inert transparent tube and having a liquid or solid reagent retained thereon, which reacts with a naturally volatile component of the liquid or solid specimen; and
      ii. means for supporting said absorbant element in its tube in spaced relation from the bottom of the container whereby vapor emitted from the liquid or solid specimen at the bottom of the container contacts the reagents to provie a visual indication thereof, but the bulk specimen does not come in contact with the reagents.

2. A device as claimed in claim 1 in which the container comprises a tubular member open at one end that can directly receive the bulk specimen to be analyzed for a volatile component without the bulk specimen passing through the detector device.

3. A device as claimed in claim 2 which includes a hollow tubular member open at both ends, and received in telescoping relation closely fitting within the container and occupying virtually the entire upper portion of the container with the lower end of said hollow tubular member spaced in a fixed position from the bottom of the container and in which the absorbant element is housed within said tubular member.

4. A device as claimed in claim 3 in which the tubular member is formed with an annular lip extending outwardly for a distance greater than the container to engage the open upper end of the container when telescoped within the container in position of use and is maintained out of contact with the volatile component to be analyzed.

5. A device as claimed in claim 3 which includes means for effecting a sealing engagement between the tubular member and container and means for displacement of the tubular member relative to the container for creating subatmospheric conditions in the space below the lower end of the tubular member within the container.

6. A device as claimed in claim 5 in which the sealing means comprises sealing elements in sealing engagement with the outer wall of the hollow tubular member and the inner wall of the container in which the seal is maintained during the movement of the hollow tubular member within the outer container.

7. A device as claimed in claim 5 in which the lower end of the container is open to enable liquid or fine grain solid specimens to be drawn into the container and a removable closure for sealing the open lower end of the container.

8. A device as claimed in claim 5 in which the means for displacement of tubular member comprises an elongate rod extending from the tubular member to beyond the open end of the container and a handle on the through extending portion.

9. A device in accordance with claim 1 or claim 2 wherein the container is heat resitant.

10. A device as claimed in claim 1 in which the container is formed of glass.

11. A device as claimed in claim 3 in which the container and tubular member are formed of glass.

* * * * *